US009486637B2

(12) United States Patent  
Greenhut et al.

(10) Patent No.: US 9,486,637 B2  
(45) Date of Patent: Nov. 8, 2016

(54) METHOD AND APPARATUS FOR ACCURATE SEPARATION OF SUPRAVENTRICULAR TACHYCARDIA FROM VENTRICULAR TACHYCARDIA DURING POSTURE CHANGES

(71) Applicant: Medtronic, Inc., Minneapolis, MN (US)

(72) Inventors: Saul E. Greenhut, Aurora, CO (US); Robert W. Stadler, Shoreview, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 158 days.

(21) Appl. No.: 14/339,833

(22) Filed: Jul. 24, 2014

(65) Prior Publication Data

US 2016/0023013 A1    Jan. 28, 2016

(51) Int. Cl.

| A61B 5/04 | (2006.01) |
| A61N 1/39 | (2006.01) |
| A61B 5/0452 | (2006.01) |
| A61N 1/362 | (2006.01) |
| A61N 1/37 | (2006.01) |
| A61B 5/0464 | (2006.01) |
| A61B 5/00 | (2006.01) |

(52) U.S. Cl.
CPC ........... *A61N 1/3987* (2013.01); *A61B 5/0464* (2013.01); *A61B 5/04525* (2013.01); *A61B 5/686* (2013.01); *A61N 1/3622* (2013.01); *A61N 1/3624* (2013.01); *A61N 1/37* (2013.01); *A61N 1/3925* (2013.01); *A61N 1/3962* (2013.01)

(58) Field of Classification Search
CPC ............ A61B 5/0402; A61B 5/04023; A61B 5/04525; A61B 5/7246
See application file for complete search history.

(56) References Cited

U.S. PATENT DOCUMENTS

| 5,193,535 A | 3/1993 | Bardy et al. |
| 5,342,404 A | 8/1994 | Alt et al. |
| 5,354,316 A | 10/1994 | Keimel |

(Continued)

FOREIGN PATENT DOCUMENTS

| AU | 2010201351 A1 | 4/2010 |
| AU | 2012265575 A1 | 1/2013 |

(Continued)

OTHER PUBLICATIONS

Zhang, "A Beat-Morphology Matching Scheme for Cardiac Sensing and Event Detection", U.S. Appl. No. 13/826,097, filed Mar. 14, 2013, 37 pages.

(Continued)

*Primary Examiner* — Christopher D Koharski  
*Assistant Examiner* — Natasha Patel

(57) ABSTRACT

An implantable medical device system includes an implantable cardioverter defibrillator (ICD) for detecting and treating ventricular tachycardia (VT). The ICD includes a sensing module for sensing a cardiac signal from selected cardiac signal sensing vectors. A control module generates morphology templates of the cardiac signals for multiple patient postures for each of the available sensing vectors. A cardiac signal received during an unknown cardiac rhythm is compared to the morphology templates without determining a current posture of the patient. The unknown cardiac rhythm is detected and classified as supraventricular tachycardia in response to the cardiac signal matching at least one of the morphology templates.

21 Claims, 6 Drawing Sheets

(56) References Cited

U.S. PATENT DOCUMENTS

| | | |
|---|---|---|
| 5,447,519 A | 9/1995 | Peterson |
| 5,545,186 A | 8/1996 | Olson et al. |
| 5,593,431 A | 1/1997 | Sheldon |
| 5,865,760 A | 2/1999 | Lidman et al. |
| 6,044,297 A | 3/2000 | Sheldon et al. |
| 6,104,949 A | 8/2000 | Pitts Crick et al. |
| 6,393,316 B1 | 5/2002 | Gillberg et al. |
| 6,397,100 B2 | 5/2002 | Stadler et al. |
| 6,745,068 B2 | 6/2004 | Koyrakh et al. |
| 6,975,904 B1 | 12/2005 | Sloman |
| 7,031,771 B2 | 4/2006 | Brown et al. |
| 7,336,999 B1 | 2/2008 | Koh |
| 7,496,409 B2 | 2/2009 | Greenhut et al. |
| 7,706,869 B2 | 4/2010 | Cao et al. |
| 7,894,894 B2 | 2/2011 | Stadler et al. |
| 7,904,153 B2 | 3/2011 | Greenhut et al. |
| 7,941,214 B2 | 5/2011 | Kleckner et al. |
| 7,991,471 B2 | 8/2011 | Ghanem et al. |
| 7,996,070 B2 | 8/2011 | van Dam et al. |
| 8,050,751 B2 | 11/2011 | Zhang et al. |
| 8,068,901 B2 | 11/2011 | Ghanem et al. |
| 8,160,684 B2 | 4/2012 | Ghanem et al. |
| 8,301,233 B2 | 10/2012 | Zhang et al. |
| 8,321,016 B2 | 11/2012 | Holmström |
| 8,332,022 B2 | 12/2012 | Brown et al. |
| 8,380,295 B2 | 2/2013 | Greenhut et al. |
| 8,391,944 B2 | 3/2013 | O'Brien et al. |
| 8,428,697 B2 | 4/2013 | Zhang et al. |
| 8,428,718 B2 | 4/2013 | Stadler et al. |
| 8,428,720 B2 | 4/2013 | Corbucci et al. |
| 8,435,185 B2 | 5/2013 | Ghanem et al. |
| 8,437,842 B2 | 5/2013 | Zhang et al. |
| 8,868,165 B1 * | 10/2014 | Nabutovsky ........... A61B 5/053 600/515 |
| 2002/0091331 A1 | 7/2002 | Onoda et al. |
| 2003/0097153 A1 | 5/2003 | Bardy et al. |
| 2006/0111643 A1 | 5/2006 | Cazares et al. |
| 2007/0156057 A1 | 7/2007 | Cho et al. |
| 2008/0132965 A1 | 6/2008 | Ostroff et al. |
| 2008/0188901 A1 | 8/2008 | Sanghera et al. |
| 2009/0054796 A1 | 2/2009 | Sanghera et al. |
| 2009/0054938 A1 | 2/2009 | Ostroff et al. |
| 2009/0228057 A1 | 9/2009 | Allavatam et al. |
| 2010/0274148 A1 | 10/2010 | Zhang et al. |
| 2010/0331903 A1 | 12/2010 | Zhang et al. |
| 2010/0331904 A1 | 12/2010 | Warren et al. |
| 2011/0098775 A1 | 4/2011 | Allavatam et al. |
| 2012/0089032 A1 | 4/2012 | Park et al. |
| 2012/0101392 A1 | 4/2012 | Bhunia et al. |

FOREIGN PATENT DOCUMENTS

| | | |
|---|---|---|
| AU | 2013267073 A1 | 1/2014 |
| EP | 2025363 A2 | 2/2009 |
| WO | 2004105871 A1 | 12/2004 |
| WO | 2006039693 A1 | 4/2006 |
| WO | 2008153450 A1 | 12/2008 |
| WO | 2009131976 A1 | 10/2009 |

OTHER PUBLICATIONS (PCT/US2015/037118) PCT Notification of Transmittal of the International Search Report and the Written Opinion of the International Searching Authority, Mailed Sep. 8, 2015, 13 pages.

* cited by examiner

METHOD AND APPARATUS FOR ACCURATE SEPARATION OF SUPRAVENTRICULAR TACHYCARDIA FROM VENTRICULAR TACHYCARDIA DURING POSTURE CHANGES

TECHNICAL FIELD

The disclosure relates generally to implantable medical devices and, in particular, to a method and apparatus for discriminating supraventricular tachycardia (SVT) from ventricular tachycardia (VT) when cardiac signal morphology changes with patient posture.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), provide therapeutic electrical stimulation to or monitor the heart of the patient via electrodes carried by one or more implantable leads. The leads may be transvenous, i.e., implanted in the heart through one or more veins, sometimes referred to as endocardial leads. Other leads may be non-transvenous leads implanted outside the heart. In either case, the electrical stimulation provided by the IMD may include signals such as pacing pulses, cardioversion shocks or defibrillation shocks to address abnormal cardiac rhythms such as bradycardia, tachycardia or fibrillation.

In some cases, the IMD senses signals representative of intrinsic depolarizations of the heart and analyzes the sensed signals to identify normal or abnormal rhythms. Upon detection of an abnormal rhythm, the device may deliver an appropriate electrical stimulation signal or signals to restore or maintain a more normal rhythm. For example, an IMD may deliver pacing pulses to the heart upon detecting tachycardia or bradycardia, and deliver cardioversion or defibrillation shocks to the heart upon detecting tachycardia or fibrillation.

SUMMARY

In general, the disclosure is directed to techniques for discriminating between treatable heart rhythms, e.g., ventricular tachycardia (VT), and non-treatable heart rhythms, e.g., supra-ventricular tachycardia (SVT), of a heart of a patient. An implantable cardioverter defibrillator (ICD) operating in accordance with the techniques performs a morphology analysis for detecting and discriminating VT and SVT based on cardiac signal templates acquired during different patient postures without necessarily requiring a posture sensor.

To reduce the likelihood of misclassification of the rhythm, the ICD generates and stores cardiac electrical signal templates for multiple patient body postures for all available cardiac signal sensing vectors. The ICD may reduce the number of generated templates to a reduced number of stored templates in response to comparing the templates generated for a given sensing vector to each other. In one example, the ICD compares the morphology of a cardiac electrical signal sensed during an unknown rhythm to at least a portion of the stored templates. The ICD classifies the unknown rhythm as VT or SVT based on the comparison.

In one example, the disclosure provides a method comprising sensing a first cardiac signal during a known cardiac rhythm from each of a plurality of available sensing vectors; generating, for each of the plurality of available sensing vectors, a plurality of morphology templates of the first cardiac signal for each of a plurality of patient postures; sensing a second cardiac signal during an unknown cardiac rhythm using one or more of the plurality of available sensing vectors; comparing the second cardiac signal to at least a portion of the plurality of morphology templates without determining a current posture of the patient, and detecting the unknown cardiac rhythm as supraventricular tachycardia in response to the second cardiac signal matching at least one of the plurality of morphology templates.

In another example, the disclosure provides an implantable medical device comprising a sensing module coupled to a plurality of electrodes defining a plurality of available sensing vectors, a therapy delivery module coupled to the plurality of electrodes and a control module. The control module is configured to generate, for each of the plurality of available sensing vectors, a plurality of morphology templates of a first cardiac signal received from the sensing module for each of a plurality of patient postures, the first cardiac signal received during a known cardiac rhythm; receive a second cardiac signal from the sensing module during an unknown cardiac rhythm using one or more of the plurality of available sensing vectors; compare the second cardiac signal to at least a portion of the plurality of morphology templates without determining a current posture of the patient, and detect the unknown cardiac rhythm as supraventricular tachycardia in response to the second cardiac signal matching at least one of the plurality of morphology templates.

In another example, the disclosure provides a computer-readable storage medium comprising instructions that, when executed by a control module in an implantable medical device, cause the implantable medical device to sense a first cardiac signal during a known cardiac rhythm from each of a plurality of available sensing vectors; generate, for each of the plurality of available sensing vectors, a plurality of morphology templates of the first cardiac signal for each of a plurality of patient postures; sense a second cardiac signal during an unknown cardiac rhythm using one or more of the plurality of available sensing vectors; compare the second cardiac signal to at least a portion of the plurality of morphology templates without determining a current posture of the patient and detect the unknown cardiac rhythm as supraventricular tachycardia in response to the second cardiac signal matching at least one of the plurality of morphology templates.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
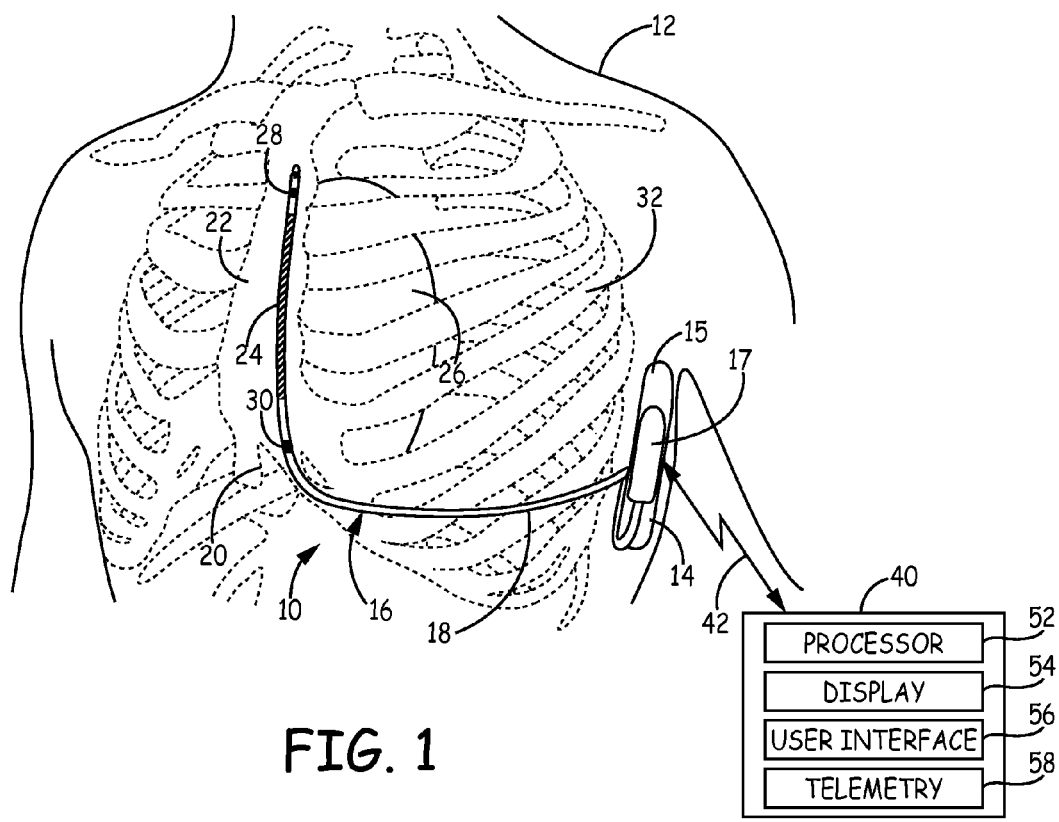
FIG. 1 is a conceptual diagram of a patient implanted with an example IMD system that includes an ICD coupled to a subcutaneous defibrillation lead.

In general, this disclosure describes techniques for distinguishing between treatable arrhythmias and non-treatable arrhythmias. Treatable arrhythmias refer to abnormal heart rhythms for which stimulation therapy is delivered to one or both of the ventricles. Treatable arrhythmias may include ventricular tachycardia (VT) or ventricular fibrillation (VF). Treatable arrhythmias generally pose an immediate danger to the patient and therapy is needed in order to ensure the safety of the patient. Non-treatable arrhythmias, on the other hand, refer to abnormal heart rhythms that typically do not require stimulation therapy to be delivered to either of the ventricles. Non-treatable arrhythmias may include supra-ventricular tachycardia (SVT), which includes sinus tachycardia, atrial tachycardia (AT), atrial fibrillation (AF), atrial flutter, atrioventricular nodal reentrant tachycardia (AVNRT), atrioventricular reciprocating tachycardia (AVRT), or the like. Non-treatable arrhythmias do not generally pose an immediate danger to the patient. As such, non-treatable arrhythmias may go untreated, i.e., no stimulation therapy is delivered to the heart. In other instances, non-treatable arrhythmias may be treated using stimulation therapy, but the stimulation therapy is not delivered to the ventricles of the patient.

Accurately determining whether the heart rhythm is treatable or non-treatable prevents inadvertent delivery of therapy to a ventricle of the patient when no therapy to the ventricle is necessary (e.g., in the case of a rhythm mischaracterized as a treatable arrhythmia) or withholding stimulation therapy when the therapy to the ventricle is necessary (e.g., in the case of a rhythm mischaracterized as a non-treatable arrhythmia). Unnecessary delivery of stimulation therapy to the patient may be uncomfortable for the patient, needlessly depletes the power source of the medical device and, in some patients or circumstances, can induce more dangerous arrhythmias.

Some ICD systems rely on electrodes that are implanted outside the heart for receiving electrocardiogram (ECG) signals that are used to detect and discriminate heart rhythms. These ICD systems may be desirable for some patients because the elimination of transvenous leads eliminates the need to advance catheters and leads into the blood vessels and heart of the patient and reduces the risk of serious infection by eliminating the pathway for infection from a subcutaneous pocket to the patient's heart. The ECG is sensed from electrodes implanted outside the cardiovascular system, for example subcutaneously, submuscularly, or substernally, in some examples. The ECG obtained from electrodes implanted outside the cardiovascular system may be subject to morphology changes due to changes in patient posture.

An ICD according to the present disclosure includes a tachyarrhythmia detection module for discriminating between treatable and untreatable rhythms using morphology analysis based on ECG templates acquired during different patient postures without necessarily requiring a posture sensor. As disclosed herein, VT detection includes a comparative morphology analysis that utilizes ECG templates acquired during different patient postures to either confirm VT detection (a treatable rhythm) or detect a tachycardia episode as SVT (a non-treatable rhythm).

FIG. 1 is a conceptual diagram of a patient 12 implanted with an example IMD system 10 that includes an ICD 14 coupled to a defibrillation lead 16. Defibrillation lead 16 includes a proximal end that is connected to ICD 14 and a distal end that includes one or more electrodes. Defibrillation lead 16 is illustrated in FIG. 1 as being implanted subcutaneously, e.g., in tissue and/or muscle between the skin and the ribcage and/or sternum 22. Defibrillation lead 16 extends subcutaneously from ICD 14 toward xiphoid process 20. At a location near xiphoid process 20 defibrillation lead 16 bends or turns and extends subcutaneously superior, substantially parallel to sternum 22. Although illustrated as being offset laterally from and extending substantially parallel to sternum 22 in the example of FIG. 1, defibrillation lead 16 may be implanted over sternum 22, offset from sternum 22, but not parallel to sternum 22 (e.g., angled laterally from sternum 22 at either the proximal or distal end).

Figure 2:
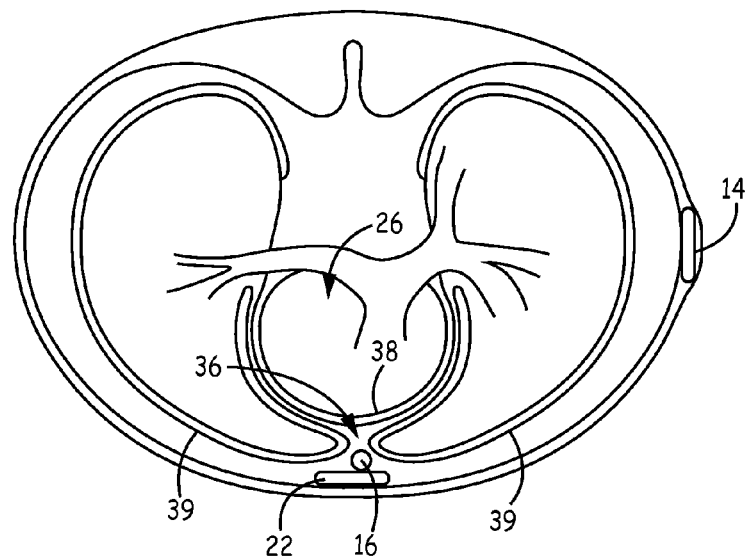
FIG. 2 is a transverse view of the patient in FIG. 1 depicting the defibrillation lead implanted in an alternate location.

In other instances, lead 16 may be implanted at other extravascular locations. As shown in a transverse view of patient 12 in FIG. 2, lead 16 may be implanted at least partially in a substernal location, e.g., between the ribcage and/or sternum 22 and heart 26. In one such configuration, a proximal portion of lead 16 extends subcutaneously from ICD 14 toward sternum 22 (not seen in the transverse view of FIG. 2) and a distal portion of lead 16 extends superior under or below the sternum 22 in the anterior mediastinum 36. Anterior mediastinum 36 is bounded laterally by pleurae 39, posteriorly by pericardium 38, and anteriorly by sternum 22.

In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 extends along the posterior side of sternum 22 substantially within the loose connective tissue and/or substernal musculature of anterior mediastinum 36. Lead 16 may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 26 and not above sternum 22 or ribcage.

In another example, ICD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of ICD 14 laterally and posterially to the patient's back to a location opposite heart 26 such that the heart 26 is generally disposed between the ICD 14 and distal electrode coil 24 and distal sensing electrode 28.

Referring again to FIG. 1, lead 16 includes an elongated lead body 18 carrying electrodes 24, 28 and 30 located along the distal portion of the length of the lead body 18. Lead body 18 insulates one or more elongated electrical conductors (not illustrated) that extend from a respective electrode 24, 28 and 30 through the lead body to a proximal connector (not shown) that is coupled to ICD 14. Lead body 16 may be formed from a non-conductive material, such as silicone, polyurethane, fluoropolymers, or mixtures thereof or other appropriate materials, and is shaped to form one or more lumens within which the one or more conductors extend. The conductors are electrically coupled to ICD circuitry, such as a therapy module or a sensing module, via connections in an ICD connector assembly 17 that includes a connector bore for receiving the proximal connector of lead 16 and associated electrical feedthroughs crossing ICD housing 15. The electrical conductors transmit therapy from a therapy module within ICD 14 to one or more of electrodes 24, 28, and 30, and transmit sensed electrical signals from one or more of electrodes 24, 28, and 30 to the sensing module within ICD 14.

Defibrillation lead 16 is shown in FIG. 1 to include a defibrillation electrode 24, which may be an elongated coil electrode, along the distal portion of defibrillation lead 16. Defibrillation lead 16 is located on lead 16 such that when ICD system 10 is implanted a therapy vector between defibrillation electrode 24 and a housing or can electrode 15 of ICD 14 is substantially through or across the ventricle(s) of heart 26.

Defibrillation lead 16 also includes one or more sensing electrodes 28 and 30, located toward the distal portion of defibrillation lead 16. In the example illustrated in FIG. 1, sensing electrodes 28 and 30 are separated from one another by defibrillation electrode 24. In other words, sensing electrode 28 is located distal to defibrillation electrode 24 and sensing electrode 30 is proximal to defibrillation electrode 24. ICD system 10 may sense electrical activity of heart 26 via one or more sensing vectors that include combinations of electrodes 28 and 30 and the housing or can electrode 15 of ICD 14. For example, ICD 14 may receive a subcutaneous ECG signal across a sensing vector between electrodes 28 and 30, a sensing vector between electrode 28 and the conductive housing or can electrode 15, a sensing vector between electrode 30 and the conductive housing or can electrode 15, or any combination of electrodes 28, 30 and the housing or can electrode 15. In some instances, ICD 14 may even sense cardiac electrical signals using a sensing vector that includes defibrillation electrode 24.

ICD 14 analyzes the electrical signals received from one or more of the sensing vectors described above to detect and treat tachyarrhythmias, such as VT or VF. ICD 14 may deliver one or more cardioversion or defibrillation shocks via defibrillation electrode 24 in response to detecting VT or VF. ICD 14 may also provide pacing therapy, such as anti-tachycardia pacing (ATP) and/or post-shock pacing after a cardioversion or defibrillation shock when pacing capabilities are available.

ICD 14 includes a housing 15, also referred to herein as housing electrode or can electrode 15, which forms a hermetic seal that protects internal electronic components of ICD 14. The housing 15 may be formed of a conductive material, such as titanium, titanium alloy, or other conductive material to serve as an electrode. Housing 15 may function as a "can electrode" since the conductive housing or a portion thereof may be coupled to internal circuitry to be used as an indifferent or ground electrode during sensing or defibrillation shock delivery.

ICD 14 also includes connector assembly 17 (also referred to as a connector block or header) that includes electrical feedthroughs through which electrical connections are made between electrical conductors within lead 16 and electronic components included within the housing 15. As will be described in further detail herein, housing 15 may enclose one or more processors, memory devices, transmitters, receivers, sensors, sensing circuitry, therapy circuitry and other appropriate components.

The example illustrated in FIG. 1 is illustrative in nature and should not be considered limiting of the techniques described in this disclosure. In other examples, ICD 14 and one or more associated leads may be implanted at other locations. For example, ICD 14 may be implanted in a subcutaneous pocket in the right chest. In this example, defibrillation lead 16 may extend subcutaneously from the device toward the manubrium of the sternum 22 and bend or turn and extend subcutaneously or substernally inferiorly from the manubrium of the sternum, substantially parallel with the sternum.

The techniques disclosed herein may be implemented in numerous ICD and electrode configurations that include one or more housing-based electrodes and/or one or more lead-based electrodes for enabling sensing of an ECG signal across one or more sensing vectors and for delivering electrical stimulation therapies to heart 26. The IMD system 10 is an extravascular IMD system because lead 16 is positioned in an extravascular location outside the blood vessels, heart 26 and pericardium 38. It is understood that while ICD 14 and lead 16 may be positioned between the skin and a muscle layer of the patient 12, ICD 14 and any associated leads could be positioned in any extravascular location of the patient, such as below a muscle layer or even within the thoracic cavity.

An external device 40 is shown in telemetric communication with ICD 14 by a communication link 42. External device may include a processor 52, display 54, user interface 56 and telemetry unit 58. Processor 52 controls external device operations and processes data and signals received from ICD 14. Display 54, which may include graphical user interfaces, displays data and other information to a user for reviewing ICD operation and programmed parameters and ECG signals retrieved from ICD 14. User interface 56 which may include a mouse, touch screen, key pad or the like to enable a user to interact with external device 40 to initiate a telemetry session with ICD 14 for retrieving data from and/or transmitting data to ICD 14. Telemetry unit 58 is configured for bidirectional communication with a telemetry module included in ICD 14 and is configured to operate in conjunction with processor 52 for sending and receiving data relating to ICD functions via communication link 42.

Communication link 42 may be established between ICD 14 and external device 40 using a radio frequency (RF) link such as Bluetooth, Wi-Fi, or Medical Implant Communication Service (MICS) or other RF bandwidth. External device 40 may be embodied as a programmer used in a hospital, clinic or physician's office to retrieve data from ICD 14 and to program operating parameters and algorithms in ICD 14 for controlling ICD 14 functions. For example, external device 40 may be used to program ICD tachyarrhythmia detection parameters, such as VT and VF interval zones, the number of VT and VF intervals required to detect VT and VF, and detection criteria relating to morphology analysis of the ECG signals. External device 40 may also be used to program therapy control parameters, such as the shock energy used to terminate VT or VF. External device 40 may alternatively be embodied as a home monitor or hand held device.

The tachycardia discrimination and therapy delivery techniques disclosed herein are useful in an extravascular IMD system such as the system 10 shown in FIG. 1 that may be susceptible to posture-induced ECG morphology changes. Electrodes 28 and 30 carried by lead 16 and located in subcutaneous or substernal locations may be more susceptible to posture-induced changes in the ECG morphology than electrodes attached to or within the heart. An extravascular IMD system is less invasive and may be more easily implanted than a system including transvenous or epicardial leads. However, techniques disclosed herein may be implemented in other examples of IMD systems that include transvenous intracardiac leads and electrodes, epicardial electrodes or other lead and electrode systems. Examples of other IMD systems in which the techniques disclosed herein could be implemented for discriminating VT from SVT in the presence of posture-induced cardiac signal morphology changes are generally disclosed in U.S. Pat. No. 8,332,022 (Brown et al.) and U.S. Pat. No. 5,447,519 (Peterson), and U.S. Pat. No. 7,496,409 (Greenhut, et al.) all of which patents are incorporated herein by reference in their entirety.

Figure 3:
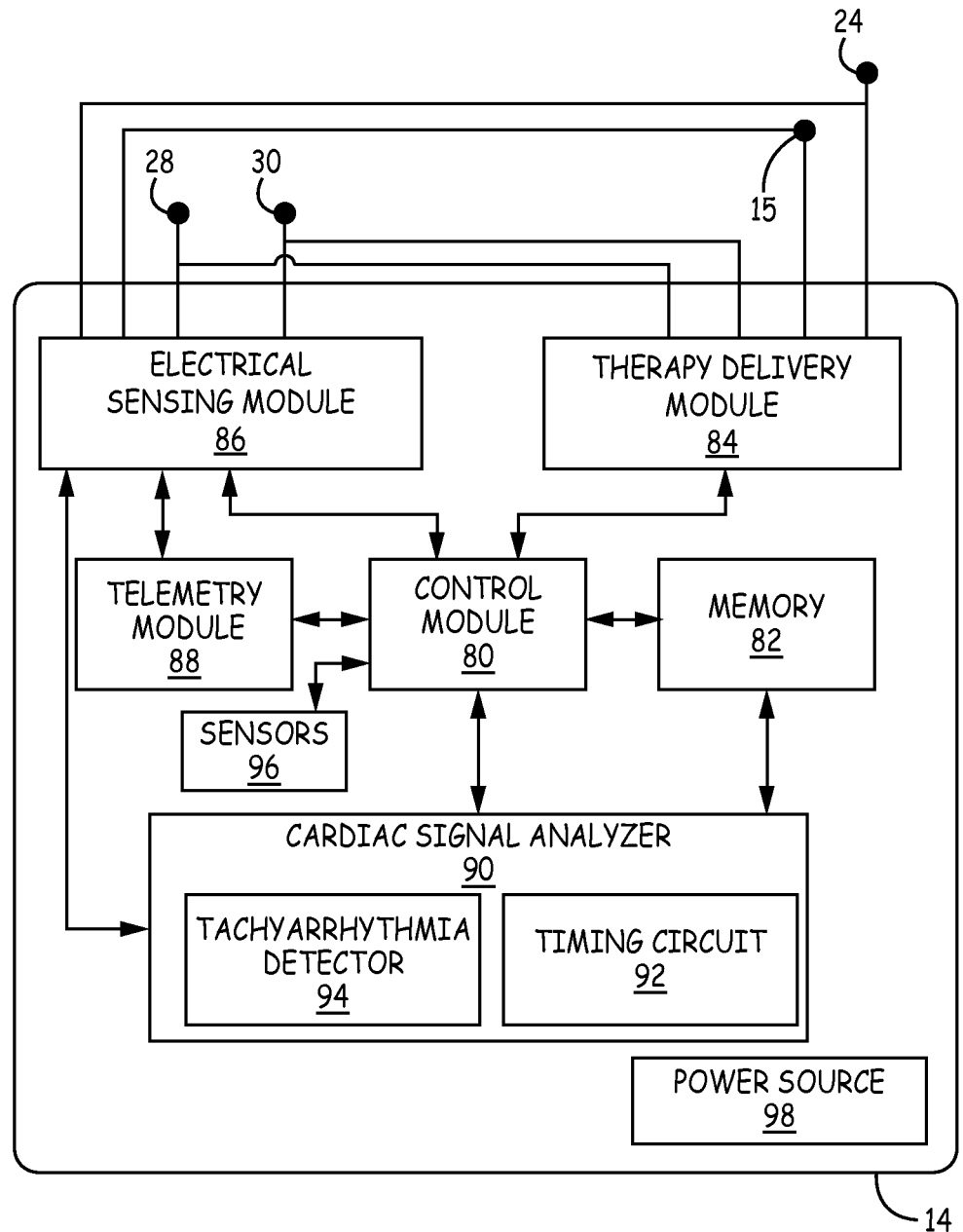
FIG. 3 is a schematic diagram of an ICD according to one embodiment.

FIG. 3 is a schematic diagram of ICD 14 according to one embodiment. The electronic circuitry enclosed within housing 15 includes software, firmware and hardware that cooperatively monitor one or more ECG signals, determine when a cardioversion-defibrillation shock is necessary, and deliver prescribed cardioversion-defibrillation therapies. In some examples, ICD 14 may be coupled to a lead, such as lead 16, carrying electrodes, such as electrodes 24, 28 and 30, positioned in operative relation to the patient's heart for delivering cardiac pacing pulses in addition to shock therapies and may therefore include the capability to deliver low voltage pacing pulses as well as the high voltage shock pulses.

ICD 14 includes control module 80, associated memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, ASICs, memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 may be implemented in control module 80 executing instructions stored in memory 82. As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality.

Control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16 (shown in FIG. 1) and housing electrode 15, which may serve as a common or ground electrode.

Electrical sensing module 86 is selectively coupled to electrodes 28, 30 and housing electrode 15 in order to monitor electrical activity of the patient's heart. Electrical sensing module 86 may additionally be selectively coupled to electrode 24. Sensing module 86 is enabled to selectively monitor one or more sensing vectors selected from the available electrodes 24, 28, 30 and 15. For example, sensing module 86 may include switching circuitry for selecting which of electrodes 24, 28, 30 and housing electrode 15 are coupled to sense amplifiers included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, 30 and housing electrode 15. For example, a sensing vector between electrodes 28 and 30 may be selected for sensing a first ECG vector on one channel and at least one additional sensing vector may be selected between one of electrodes 24, 28 and 30 paired with the housing electrode 15 and received on another sensing channel. Each sensing channel may be configured to amplify and filter the ECG to improve the signal quality for sensing cardiac events, e.g., R-waves.

Each sensing channel of sensing module 86 may include a sense amplifier for receiving the ECG signals developed across the selected electrodes. The sense amplifiers pass sense event signals to control module 80 and/or cardiac signal analyzer 90. For example, R-wave sense signals may be passed to tachyarrhythmia detector 94 and timing circuit 92 of cardiac signal analyzer 90 when a received ECG signal crosses a sensing threshold, which may be an auto-adjusting sensing threshold in some instances.

Sensing module 86 may include an analog-to-digital converter for providing a digital ECG signal to control module 80 and/or cardiac signal analyzer 90. In one example, two sensing channels are provided for receiving an ECG from a first sensing vector between electrodes 28 and 30 and a second sensing vector selected from either electrode 28 or electrode 30 paired with the housing electrode 15. The two ECG signals are converted to a multi-bit digital signal by sensing module 86 and provided to tachyarrhythmia detector 94 for performing ECG morphology analysis as described herein.

Cardiac signal analyzer 90 includes a tachyarrhythmia detector 94 for detecting and discriminating SVT, VT and VF and timing circuit 92. Timing circuit 92 may include various timers and/or counters for measuring time intervals, such as RR intervals, and setting time windows such as morphology template windows or morphology analysis windows relative to R-wave sense signals or for performing other timing related functions of cardiac signal analyzer 90.

The timing of R-wave sense signals received from sensing module 86 is used by timing circuit 94 to measure RR intervals. Tachyarrhythmia detector 94 may count RR intervals measured by timing circuit 92 that fall into different rate detection zones for determining a ventricular rate or preforming other rate- or interval-based assessment for detecting ventricular tachyarrhythmia.

Electrical sensing module 86 additionally or alternatively provides digitized ECG signals to cardiac signal analyzer 90 for use in detecting tachyarrhythmia based on signal morphology. Examples of algorithms that may be performed by ICD 14 for detecting, discriminating and treating tachyarrhythmia and adapted to include techniques described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

The detection algorithms are highly sensitive and specific for the presence or absence of life threatening VT and VF. Therapy delivery module 84 includes a high voltage (HV) therapy delivery module including one or more HV output capacitors and, in some instances, a low voltage therapy delivery module. When a malignant tachycardia is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using defibrillation electrode 24 and housing electrode 15. Timing circuit 92 may be used to control R-wave synchronized shock pulses delivered by therapy delivery module 84.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by processing and control module 80 to apply or withhold a therapy.

Certain steps in the performance of the VT detection algorithm described herein are cooperatively performed in control module 80, including memory 82, cardiac signal analyzer 90 and stored detection criteria and other control parameters that may be programmed into memory 82 via telemetry module 88. Initial detection of VT or VF may be determined in the tachyarrhythmia detector 94 as a function of the time intervals between R-wave sense event signals that are output from sensing module 86. Discrimination of VT and SVT is performed by tachyarrhythmia detector 94 through analysis of the morphology of the sensed ECG signal(s) after an initial RR interval-based VT detection is made. Digital ECG signals received from one or more sensing channels of sensing module 86 may be stored in memory 82. Tachyarrhythmia detector 94 employs the digitized ECG signals stored in memory 82 in conjunction with morphology analysis.

As described below, digitized ECG signals are acquired during a stable heart rhythm (stable rate and morphology) and used by cardiac signal analyzer 90 to generate morphology templates for each available sensing vector, for example three vectors between electrodes 28 and 30, between electrode 28 and housing electrode 15, and between electrode 30 and housing electrode 15, respectively. A morphology template for each sensing vector is generated for multiple patient postures.

Morphology analysis performed by tachyarrhythmia detector 94 includes comparing one or more ECG signals sensed using selected sensing vectors to morphology templates stored in memory 82 for the respective sensing vector. Some aspects of sensing and processing subcutaneous ECG signals are generally disclosed in commonly-assigned U.S. Pat. No. 7,904,153 (Greenhut, et al.), hereby incorporated herein by reference in its entirety.

A morphology template is generated for each available sensing vector for at least two different patient postures, for example sitting and lying. A morphology template may be an ensemble averaged waveform obtained from a predetermined number of cardiac cycles. A template window may be defined relative to R-wave sense signals produced by electrical sensing module 86. The ECG signal may be ensemble averaged across multiple template windows to obtain a waveform template for a given sensing vector and patient posture. Morphology templates may be updated periodically. Methods for generating and updating a morphology template and making template comparison performed by ICD 14 may include techniques generally disclosed in U.S. Pat. No. 6,745,068 (Koyrakh, et al.), U.S. Pat. No. 7,706,869 (Cao, et al.), and U.S. Pat. No. 8,428,697 (Zhang, et al.), all of which are incorporated herein by reference in their entirety.

A morphology analysis is performed by tachyarrhythmia detector 94 using the stored templates to determine a morphology matching score or other metric of the correlation between an ECG signal received by sensing module 86 during an unknown heart rhythm and a template generated by cardiac signal analyzer 90 during a known sinus rhythm and stored in memory 82. Numerous methods may be used to determine a morphology matching score that indicates the similarity or correlation between an ECG signal during an unknown rhythm and a template obtained during sinus rhythm. In one example, determining a morphology matching score may include determining a waveform area difference between the ECG signals received from the selected sensing vectors during an unknown cardiac rhythm and morphology templates stored for the selected sensing vectors. A normalized area waveform difference may be determined as generally disclosed in U.S. patent application Ser. No. 13/826,097, filed Mar. 14, 2013, (Zhang et al.), hereby incorporated herein by reference in its entirety.

A wavelet transform method as generally disclosed in U.S. Pat. No. 6,393,316 (Gillberg et al.) is another example of a morphology matching method that may be implemented in the VT/SVT detection and discrimination techniques disclosed herein. Other morphology matching methods may be implemented by tachyarrhythmia detector 94 which compare the wave shape, amplitudes, slopes, inflection time points, number of peaks, or other features of the ECG signal, particularly of the R-wave or QRS portion of the ECG signal.

The ECG morphology received across selected sensing vectors may vary with changes in patient posture. Comparison of the ECG morphology during an unknown fast rhythm to a morphology template obtained during sinus rhythm could result in a low morphology matching score due to a change in the ECG morphology caused by a change in patient posture. A fast rhythm that is sinus tachycardia, atrial flutter, or any other SVT could potentially be falsely detected as a shockable VT, leading to unnecessary shock therapy.

By obtaining multiple morphology templates generated for each available sensing vector for different patient postures, the ECG morphology can be compared to different posture-dependent morphology templates stored in memory 82 in response to an interval-based VT detection made by cardiac signal analyzer 90. As described below, the digitized ECG signals received from sensing module 86 using selected sensing vectors during an unknown rhythm are compared to stored posture-dependent templates without requiring the use of a posture sensor to determine the actual posture of the patient. In other embodiments, sensors 96 may include a three-dimensional accelerometer for detecting changes in patient posture for use in generating templates for different patient postures. A multi-axis accelerometer that may be used for detecting patient posture is generally disclosed in U.S. Pat. No. 5,593,431 (Sheldon), hereby incorporated herein by reference in its entirety.

Telemetry module 88 includes a transceiver and antenna for communicating with external device 40 (shown in FIG. 1) using RF communication. Under the control of control module 80, telemetry module 88 may receive downlink telemetry from and send uplink telemetry to external device 40.

ECG episode data related to the detection of VT or VF and the delivery of a cardioversion or defibrillation shock may be stored in memory 82. Stored episode data is transmitted by telemetry module 88 to an external device 40 upon receipt of an interrogation command. Clinician review of episode data facilitates diagnosis and prognosis of the patient's cardiac state and therapy management decisions, including selecting programmable VT/VF detection and therapy delivery control parameters.

Figure 4:
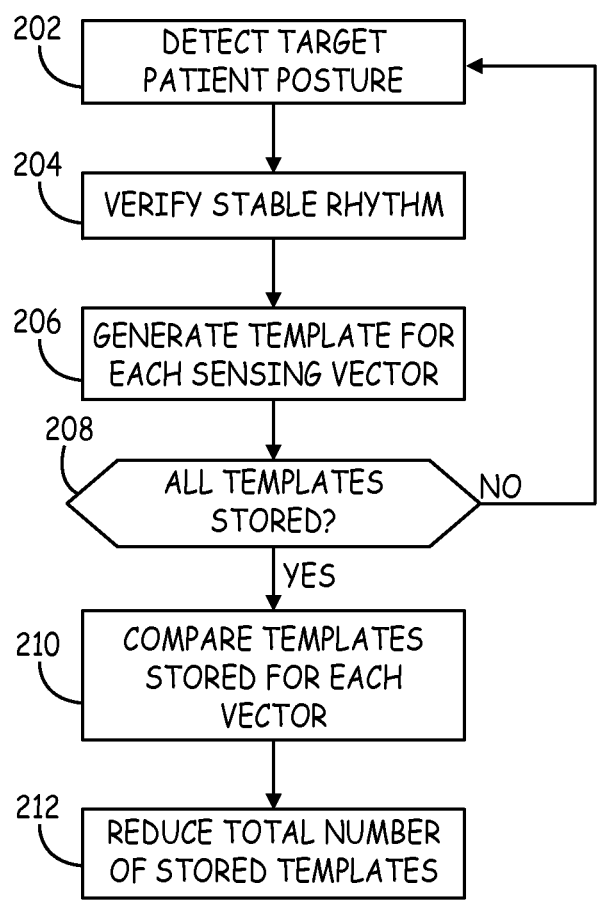
FIG. 4 is a flow chart of a method performed by an ICD for generating morphology templates for use in discriminating between VT and SVT.

FIG. 4 is a flow chart 200 of a method performed by ICD 14 for generating morphology templates for use in discriminating between VT and SVT. At block 202, a targeted patient posture is detected. An ECG morphology template is stored for multiple patient postures during a stable heart rhythm. In one example, an ECG template is generated for each of at least four patient postures including sitting (or standing but generally upright), supine, right-side lying, and left-side lying. Other postures may be used such as forward-bending, reclined sitting, prone, etc. Any desired number and combination of postures may be used. The patient may be instructed to assume the first of the desired postures, either automatically by the programmer or by a clinician, and a notification may be transmitted to the ICD 14 by user interaction with external device 40 to indicate that the patient has assumed one of the desired postures for generating a template. The ICD 14 detects that the patient is in a targeted posture for template generation in response to receiving the transmitted notification.

Prior to generating a template in response to detecting the targeted patient posture, the ICD 14 may first verify that the heart rhythm is stable at block 204 using one or more of the available sensing vectors. A stable heart rhythm may be a sinus rhythm or other supraventricular rhythm that is verified to have a stable heart rate over a required number of cardiac cycles and/or a stable ECG morphology over a required number of cardiac cycles. A stable rhythm may be normal sinus rhythm, sinus tachycardia, or an atrial paced rhythm when atrial pacing is available. In some examples, templates for each targeted posture may be generated at more than one sinus heart rate since heart rate can sometimes alter ECG morphology.

A morphology template is generated at block 206 for each available sensing vector while the patient remains in the targeted posture. For example, the first posture may be a sitting position. The ICD 14 may generate a morphology template for a sensing vector between electrodes 28 and 30, a sensing vector between electrode 28 and the housing electrode 15, and a sensing vector between electrode 30 and the housing electrode 15 while the patient remains in the sitting position. The morphology template is stored for each of the three sensing vectors for the first posture. The ICD 14 may send a notification back to the external device 40 indicating that template generation is complete for a given posture so that the process of generating templates can proceed to the next posture.

The user may have the opportunity to reject a generated template if patient movement or other potential source of ECG noise artifact occurred during the template generation. In some examples, the ICD 14 may transmit generated templates to the programmer for display and acceptance by a clinician.

The patient may then be asked to assume a second posture, e.g., a supine position. The user may interact with external device 40 to transmit a notification that causes ICD 14 to detect the next patient posture based on the notification signal and begin ECG template generation for the second posture. The process of detecting that the patient has assumed a patient posture, based on a notification signal from the programmer, verifying a stable heart rhythm and generating a morphology template for each available sensing vector is repeated for a desired number of patient postures until templates for all postures have been obtained for each sensing vector.

The methods used to generate a template at block 206 will depend in part on the particular morphology analysis algorithm being employed by the cardiac signal analyzer 90 (shown in FIG. 3). In one example, each template may represent a series of cardiac cycles that have been aligned over a template window and averaged to obtain an averaged cardiac cycle waveform that is stored as the template. In another example, features of an averaged waveform may be stored as the template. Stored features may pertain to the Q-wave, R-wave, T-wave, QRS complex, or any desired portion of a cardiac cycle. Features may include, with no limitation intended: waveform area, amplitude(s), slope(s), frequency content, signal width, number of peaks, timing sequence of maximum amplitude points and/or maximum slope points, etc. In another example, template wavelet coefficients are generated using a wavelet transform and stored as the template.

A set of morphology templates is initially generated and stored for each available sensing vector for a desired number of different patient postures, for example at least two different postures such as sitting and lying. In one example, templates are generated for at least four different postures, e.g., sitting or standing, supine, prone, right-side lying, left-side lying, forward bending, and reclined. The actual patient posture is not necessarily stored with each morphology template and may even be unknown to ICD 14. In some instances, the targeted postures are assumed to occur in a directed or prescribed order such that the templates generated for the first posture always correspond to an upright sitting position of the patient; the templates generated for the second posture always correspond to a supine position of the patient, and so on. In other instances, the order of the postures assumed by the patient may be random. In this case, however, the templates generated for each sensing vector are generated concomitantly during an assumed patient posture such that all of the first generated templates for each vector correspond to the same posture, all of the second generated templates for each vector correspond to the same posture but different than the posture corresponding to the first templates, and so on.

As such, the generated templates may be stored in ICD memory 82 with labels or numbering that corresponds to like postures across different sensing vectors. This labeling or numbering may be non-descriptive or non-identifying of what the actual patient posture was during generation of the templates. In other examples, the labeling or numbering may be descriptive or associated with the actual patient posture, e.g., based on a prescribed order of the targeted postures. The set of generated templates for each sensing vector represents the posture-dependent variation of the morphology template that may occur.

A posture sensor is not required in ICD 14 when an instruction from external device 40 is used to trigger ICD 14 to generate the morphology templates for the desired patient postures. Alternatively, a posture sensor may be included in ICD 14 for detecting different patient postures and triggering morphology template collection in an automated method. The actual patient posture, e.g., sitting, supine, prone, or side-lying, may or may not be determined; detection of a change in posture may be adequate for triggering template generation. The generated templates may be labeled as posture 1, posture 2, posture 3, etc. for each sensing vector such that templates corresponding to a common patient posture for all sensing vectors can be identified without necessarily knowing which actual patient posture a template was generated for.

Once a template is stored for each of the desired patient postures for each available sensing vector as determined at block 208, the templates generated for different postures for a given vector are compared to each other at block 210. In some cases, a particular sensing vector may be less susceptible to posture-induced variations than other sensing vectors. As such, if a template matches another template generated for the same sensing vector, the number of templates stored for the given sensing vector for use during VT/SVT detection and discrimination may be reduced at block 212.

The criteria used to determine whether two templates match each other may depend on the type of morphology analysis being performed for VT/SVT detection and discrimination. Morphology matching criteria may include as threshold percentage applied to a morphology matching score that is determined as a percentage, a percentage difference between template features, or a ratio between template features. For example a matching criterion may require template features reach a matching score threshold of 90%, or another percentage value based on the type of morphology comparison being made. In other examples, a threshold percentage difference of 10% or less between template features may be used to detect matching templates.

In one example, a normalized area waveform difference (NWAD) is determined between two templates. Sample point amplitudes of a template may be normalized by a largest amplitude sample point of the template. The NWAD between two templates is determined by subtracting normalized sample points of one template from normalized sample points of the other template after the two templates have been aligned over a morphology analysis window. A NWAD metric may be determined as ((1−AD)/TEMPLATE WA)*100 where AD is the absolute area difference between the two template waveforms and where TEMPLATE WA (waveform area) is the area of the normalized template waveform. If the NWAD metric is at least 90% (or other threshold percentage), the two templates match. Alternatively if the normalized waveform areas of two templates are within 10% of each other, the two templates match.

It is recognized that various matching criteria and morphology comparison methods may be used. In one example, if two or more templates generated for the same sensing vector during two different patient postures match based upon predetermined matching criteria, one template is retained and the other matching template(s) are discarded at block 212. In another example, if two or more templates match based on matching criteria, the matching templates may be averaged to obtain a single averaged template representative of all of the corresponding patient postures having the matching templates. By discarding any redundant templates for a given sensing vector, or reducing the total number of stored templates by averaging two or more matching templates, memory and processing time may be saved.

For example, if a left-side lying template matches the right-side lying template, one template may be discarded. If the remaining template is different than both of the supine and sitting templates, three templates may be saved in memory 82 for the given sensing vector. If all four templates for a given sensing vector match each other, a single template is stored for that sensing vector. In this way, assuming templates were collected for four different patient postures, one to four templates may be stored for each sensing vector, and the number of templates stored for one vector may be different than the number of templates stored for another vector.

In another example, the total number of generated templates may be reduced to a smaller number of stored templates at block 212 by averaging all templates generated for each available sensing vector to one averaged template for vector. Averaging all templates generated for a given sensing vector may require that comparisons between all templates for that vector meet a minimum matching score between the templates before averaging. As described below, morphology matching criteria used to detect tachycardia as SVT when an averaged template is being used may be different than morphology matching criteria used to when a non-averaged template is being used. For example a lower or relatively less stringent morphology matching threshold may be required when an averaged template is being used.

Since an averaged template may be slightly different than any of the individual templates used to produce the averaged template, a relatively lower matching threshold or more generally less stringent matching criteria may be used to determine when the ECG signal during an unknown rhythm matches the averaged template.

It is recognized that in some cases, all available sensing vectors may be highly posture dependent. None of the generated templates for a given sensing vector may match each other with a high enough matching score to reduce the total number of generated templates to a smaller number of stored templates for use in VT/SVT detection and discrimination. In this case, the number of stored templates will equal the total number of generated templates rather than a reduced number.

Once a final number of unique posture-dependent templates are stored for each sensing vector, the stored templates are available for use by a tachycardia discrimination algorithm. The process shown by flow chart 200 may be repeated periodically to update the stored templates as needed, as described below in conjunction with FIG. 7.

Figure 5:
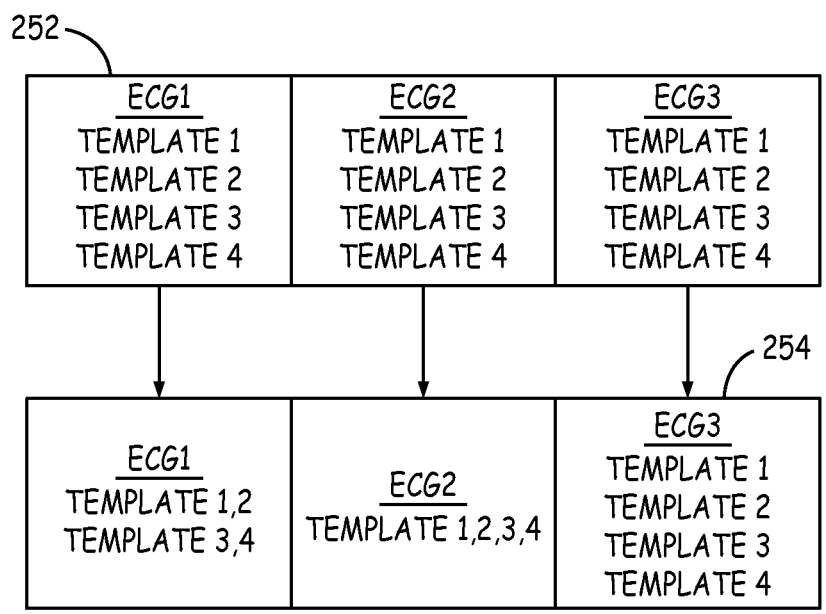
FIG. 5 is a conceptual diagram of cardiac signal templates generated and stored for multiple sensing vectors.

FIG. 5 is a conceptual diagram 250 of cardiac signal templates generated and stored for multiple sensing vectors. Block 252 represents all of the morphology templates generated for each available ECG sensing vector, referred to as ECG1, ECG2, and ECG3 in this example. ECG1 may correspond to the vector between sensing electrodes 28 and 30 shown in FIG. 1. ECG2 may correspond to the sensing vector between electrode 28 and the housing electrode 15, and ECG3 may correspond to the sensing and between electrode 30 and the housing electrode 15.

Initially, a morphology template is generated for each of a desired number of targeted patient postures, which may be referred to generically as Postures 1 through 4 for the sake of illustration. In this example of three available sensing vectors, a total of twelve morphology templates, Templates 1 through 4, are generated as indicated in block 252. The actual posture of the patient corresponding to Postures 1 through 4 need not be known. Alternatively, Posture 1 may be known to correspond to sitting, Posture 2 may be known to correspond to supine, and so on.

Template 1 through Template 4 for each sensing vector are compared to each other after generating all twelve templates for each patient posture and for each sensing vector. A reduced number of templates are stored for VT/SVT detection and discrimination, as represented by block 254. The reduced number of templates may include templates that are averaged to form a composite template representative of multiple postures. Alternatively or additionally, the number of generated templates is reduced to a stored number of templates for VT/SVT detection and discrimination by discarding templates that show no posture dependent change compared to another template for the same sensing vector.

In the illustrative example shown in FIG. 5, Template 1 and Template 2 for ECG1 may match based on a morphology matching criteria. Template 2 may be discarded and Template 1 may be retained in memory 82. Template 1 may optionally be relabeled in memory as Template 1,2 corresponding to Postures 1 and 2 to keep track of which retained template matched the discarded template. Similarly, Template 3 may match Template 4 for ECG1. Template 4 may be discarded and Template 3 may be retained. Template 3 may optionally be re-labeled as Template 3,4 in order to keep track of which retained template matched Template 4 for ECG1.

Alternatively, if two templates match, the two templates may be averaged. For example, Template 1,2 for ECG 1 stored in block 254 may be an average of the generated Template 1 and Template 2 shown in block 252. Similarly, Template 3 and Template 4 of the generated templates in block 252 may be averaged and stored as Template 3,4 in block 254.

In some examples, a combination of averaging and discarding may be used to reduce the total number of templates generated to a reduced number of stored templates utilized for VT/VT detection and discrimination. To illustrate, a comparison of Template 1 and Template 2 for ECG 1 may result in a matching score that is greater than a first template matching threshold, for example a matching score of 95%. When two templates match with a matching threshold greater than the first matching threshold, one template is discarded. Template 3 and Template 4 may match with a matching score that is less than the first matching threshold but greater than a second template matching threshold, for example a matching threshold of 90%. Templates 3 and 4 may be averaged to generate Template 3,4 representative of both templates. Template 3,4 may be considered a composite template of the two templates.

In the example shown in FIG. 5, Templates 1 through 4 for ECG 2 are reduced to a single template. All four templates may match each other according to template morphology matching criteria, for example a matching score that exceeds a template matching threshold. Templates 2, 3, and 4 may be discarded and Template 1 retained. Template 1 may optionally be re-labeled as Template 1,2,3,4 corresponding to all four patient postures. Alternatively, Template 1,2,3,4 may be an average of all four of Templates 1 through 4 generated for ECG2 in block 252. The generated Templates 1 through 4 may be verified to match each other according to matching criteria, e.g., matching scores exceeding a predetermined minimum matching threshold, prior to averaging. In yet another alternative, some of Templates 2, 3, 4, such as those that exceed a first template matching threshold (e.g., a matching score of 95%), may be discarded while the remaining ones of Templates 2, 3, 4, such as those that are less than the first matching threshold but greater than a second template matching threshold (e.g., a matching threshold of 90%) may be averaged.

In the illustrative example, Templates 1 through 4 generated for ECG3 do not match each other according to template morphology matching criteria. As such, all four templates are stored in block 254 for use in a VT/SVT detection and discrimination algorithm. Reducing the total number of templates generated for each patient posture for all available sensing vectors to a reduced number of stored templates used to compare to ECG signals from corresponding sensing vectors during an unknown rhythm may result in a different number of templates stored for each vector as shown in FIG. 5.

Labeling of the templates stored in block 254 according to a descriptive or non-descriptive label is optional. As described below, in some examples the templates for a given posture, whether that posture is known or unknown, are treated as a group such that if two or more sensing vectors are being used to acquire ECG signals for detecting VT, the templates corresponding to the same posture, for example Posture 1, are initially used for comparing to the unknown ECG signals from the respective sensing vectors. If none (or less than a required minimum number) of the first group of templates corresponding to Posture 1 match the corresponding ECG signal during the unknown rhythm, a next group of templates may be selected for comparison to the ECG signal during the unknown rhythm. The next group of templates may all correspond to Posture 2. In some cases, the next group of templates may include templates that were in the first group if the number of stored templates has been reduced from the total number of generated templates. In the example of FIG. 5, the first group of templates may be selected from ECG1 Template 1,2; ECG2 Template 1,2,3,4 and ECG3 Template 1.

The second group of templates may be selected from ECG1 Template 1,2; ECG2 Template 1,2,3,4 and ECG3 Template 2. Any templates that correspond to more than one posture do not necessarily need to be compared repeatedly as the algorithm advances through different template groups corresponding to different postures. For example, ECG1 Template 1,2 and ECG2 Template 1,2,3,4 that appear in both the first group for Posture 1 and the second group for Posture 2 may be compared again to the respective ECG sensing vector signal or the previous comparison result may be used to avoid redundant comparisons and save processing time. If none (or less than a required minimum number) of the posture 2 templates match the ECG signal for the respective sensing vector, the posture templates corresponding to Posture 3 may be selected, and so on. Knowledge of the actual patient posture corresponding to Posture 1, Posture 2, Posture 3 and Posture 4 is not required.

Figure 6:
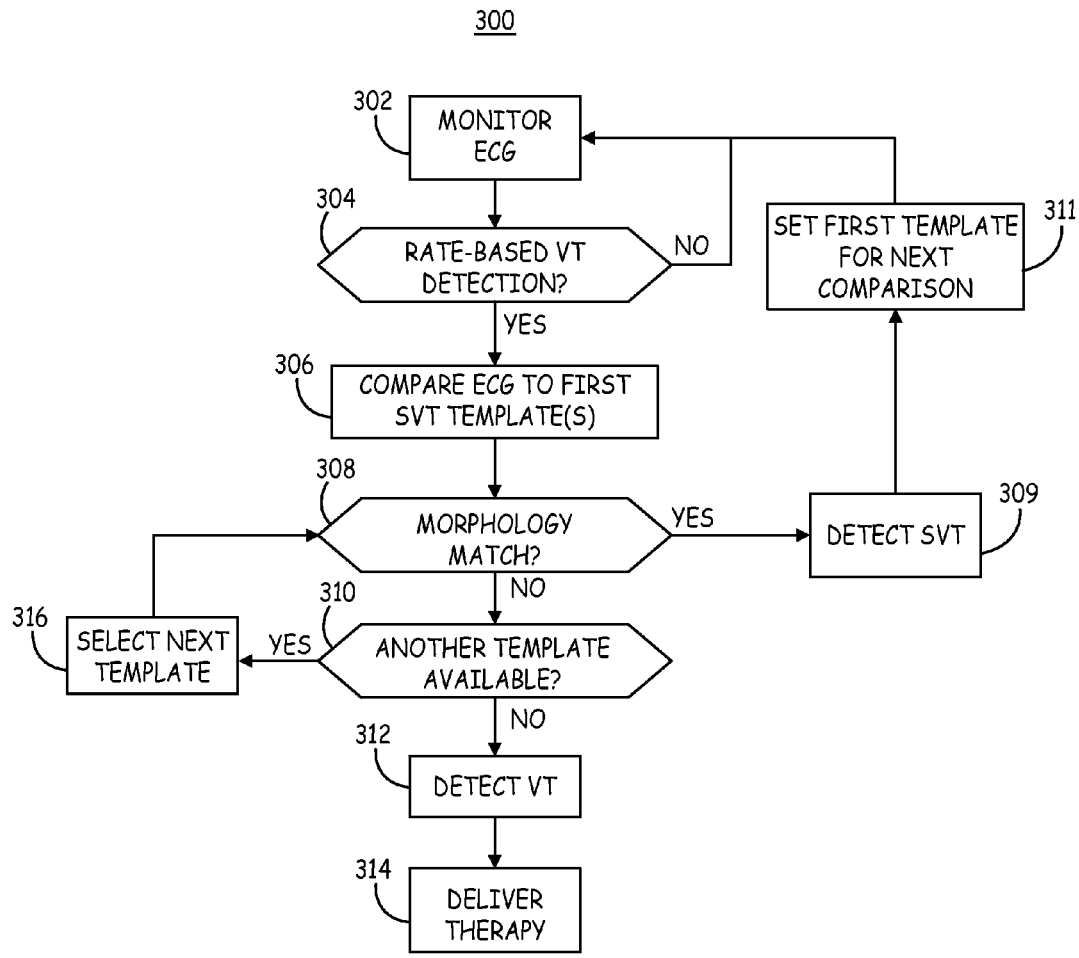
FIG. 6 is a flow chart of a method for discriminating between VT and SVT according to one example.

FIG. 6 is a flow chart 300 of a method for discriminating between VT and SVT according to one example. At block 302, an ECG signal is received across one or more selected sensing vectors. ICD 14 may be configured with two sensing channels and may select two out three available sensing vectors, such as two out of ECG1, ECG2 and ECG3 as described above in conjunction with FIG. 5. However, more or fewer sensing vectors may be utilized.

In some examples, VT is initially detected based on heart rate. R-wave sense signals are produced by the ICD sensing module 86 for each received ECG signal. RR intervals are determined by the cardiac signal analyzer 90 in response to R-wave sense signals. RR intervals are used at block 304 to detect VT according to rate or interval-based VT detection criteria. For example, VT may be detected based on a required number of intervals to detect (NID) falling into a programmed VT interval range. To illustrate, a VT detection interval range may include RR intervals less than or equal to 360 ms and greater than 320 ms. A ventricular fibrillation detection interval (FDI) range may be defined as RR intervals less than or equal to 320 ms. The VT NID may be set to 12 consecutive intervals, 24 consecutive intervals or another required number of VT detection intervals. If the required number of consecutive RR intervals are in the VT detection interval range, a preliminary VT detection may be made.

In other examples, primary VT detection criteria used at block 304 may include a prioritized set of inter-related rules pertaining to cardiac intervals, interval patterns and or morphology; rate onset; stability; gross morphology detection criteria or any combination thereof. Various examples of VT detection criteria that may be used as primary detection criteria at block 304 are disclosed in the above-incorporated patents, such as U.S. Pat. No. 5,545,186 (Olson, et al.), U.S. Pat. No. 7,031,771 (Brown, et al.), U.S. Pat. No. 8,160,684 (Ghanem, et al.), and U.S. Pat. No. 8,437,842 (Zhang, et al.).

If VT detection is made based on RR intervals or other primary detection criteria at block 304, a comparative morphology analysis of the unknown rhythm is performed at block 306 before confirming the VT rhythm classification and delivering a VT therapy. The morphology analysis is performed to determine if the morphology of the received ECG signals during the unknown rhythm matches a morphology template stored for the respective ECG sensing vectors. The first template compared to the ECG signal for each sensing vector during the unknown rhythm may be any one of the templates stored for a given vector. As indicated above, when more than one ECG signal is being monitored, the templates stored for the same posture for each sensing vector may be used to compare to the unknown ECG signal for determining a morphology matching score.

In one example, the actual patient posture corresponding to the initial set of templates selected for each sensing vector is unknown other than it is the same posture for each of the templates. The actual patient posture at the time of the rate-based VT detection need not be determined. The actual patient posture at the time of the rate-based VT detection may or may not match the posture corresponding to the first set of templates used at block 306.

In another example, the actual patient posture associated with the initial template used at block 306 is known. For example, the templates stored for each ECG sensing vector for an upright sitting posture may be selected first at block 306 to be compared to the ECG signal for each sensing vector. The actual current posture of the patient, however, need not be determined and may or may not be an upright sitting position.

If the morphology of the ECG signal during the unknown rhythm matches the first stored template for at least one selected sensing vector, as determined at block 308, the rate-based VT detection is classified as SVT at block 309. In some instances, a "gray zone" may be defined for SVT detection criteria. A gray zone is a borderline range of a matching threshold or other matching criterion. If only one template out of the selected sensing vectors meets the SVT detection criteria but is within the gray zone of a morphology matching criterion, all other selected sensing vector templates may be required to match the unknown ECG signal according to some minimum matching criteria. In other words, if one sensing vector satisfies the SVT detection criteria but only within the gray zone, and one or more other templates for the other selecting sensing vector(s) is very poorly correlated to the unknown signal, SVT is not detected.

To illustrate, SVT detection criteria may include an SVT morphology matching score threshold of 70% and a gray zone of 60% to 70%. When a single morphology matching score reaches the SVT morphology matching score threshold of 70%, SVT is detected regardless of matching scores between other templates for other sensing vectors. However, when a single morphology matching score is within the gray zone from 60% up to 70%, SVT is detected only when all other selected ECG sensing vectors result in a morphology matching score greater than a predefined minimum matching threshold, e.g., greater than 20%. If two ECG sensing vectors are selected and one template results in a matching score in the gray zone, and the other template for the other selected sensing vector results in a matching score below the minimum matching threshold, e.g., below 20%, the SVT detection criteria are not met. The very low matching score of the second template and only a borderline match of the first template do not support SVT detection. The use of a gray zone in SVT and VT detection criteria is generally disclosed in the above-incorporated U.S. Pat. No. 8,437,842 (Zhang, et al.).

In other examples, a match between the ECG signal and morphology templates from at least two (or all) selected sensing vectors is required to classify the rhythm as SVT. In one case, all templates for a particular posture may be required to match the ECG signal for each respective selected sensing vector in order to detect SVT. In another case, SVT is detected if at least one template stored for each selected sensing vector matches the unknown ECG signal, regardless of whether the corresponding postures for the matching templates are the same postures.

A morphology match at block 308 may be based on predefined SVT detection criteria. SVT detection criteria used to determine a match between an unknown ECG signal morphology and a stored template may or may not be same criteria used to identify matching morphology templates for reducing the total number of generated templates to a smaller number of stored templates as described above in conjunction with FIGS. 4 and 5. SVT detection criteria may include a lower morphology matching score threshold than morphology matching criteria used for identifying matching templates. For example, morphology matching criteria used to reduce a number of stored templates may include a morphology matching score of 90% between templates, whereas SVT detection criteria may require a morphology matching score of 60%.

SVT detection criteria, e.g., the actual values defined as morphology matching score thresholds, may vary between embodiments based on the type of morphology analysis being performed and may be programmable by a clinician or other user. Different SVT detection criteria may be applied to different stored templates in some examples. For example, a lower morphology matching score threshold may be applied to a stored template that represents an average of two or more generated templates than a morphology matching score threshold that is applied to a stored template that has not been averaged with any other generated templates. Accordingly, when templates associated with a common posture for each sensing vector are selected at block 306 for comparison to the ECG signal of the unknown rhythm, appropriate SVT detection criteria is also selected for use at block 308 to determine if the templates satisfy the SVT detection criteria.

The stored templates are referred to as SVT templates in block 306 because the templates represent the ECG signal morphology when ventricular depolarization is conducted from the atria and not arising from the ventricle. A morphology match at block 308 therefore indicates the rhythm is supraventricular. No further morphology analysis is required, and VT therapy is not delivered. ECG monitoring continues by returning to block 302.

If SVT is detected, the ICD 14 may select which of the templates will be used as the first template(s) in a subsequent comparison at block 311. For example, the first templates used in a subsequent comparison may be the group of templates stored for the posture that resulted in a matching template and led to the SVT detection. In another example, the ICD 14 may determine which stored template for each sensing vector results in the highest matching score and set that template as the first template to use in subsequent comparisons. This determination may include comparing all stored templates to the ECG signal for each selected sensing vector. In the case in which the ECG matches a template before all templates are compared, this determination may include comparing the ECG to the remainder of the templates. The template resulting in a highest morphology matching score may be selected at block 311 as the first template to be used the next time a morphology comparison is performed at block 306. It is expected that the highest matching template for one sensing vector will correspond to the same patient posture as the highest matching template for any other selected sensing vectors.

In some cases, however, templates for two different postures may result in the highest morphology matching scores for two different sensing vectors. In this case, a third ECG acquired from a third sensing vector may be compared to each of its respective morphology templates to determine which template results in the highest morphology matching score. The first templates selected at block 311 for the next morphology comparison (block 306) may be for a posture associated with the templates having the highest matching scores for a majority of all available sensing vectors, even if not all of the sensing vectors in the majority are the vectors selected for receiving ECG signals at block 302.

For example, assuming ECG1 and ECG2 are selected for ECG monitoring at block 302, if Template 1 for ECG1 produces the highest matching score at block 311 out of all the templates stored for ECG 1, but Template 2 produces the highest matching score for ECG2 out of all the templates stored for ECG2, there is a conflict between the associated postures for highest matching templates between the two selected ECG vectors. In this case, the ECG3 signal may be compared to all of the templates stored for ECG3 to determine a template having the highest matching score. If the highest matching template for ECG3 is associated with the same posture as either of the highest matching templates for ECG1 or ECG2, the templates for that posture are set as the first templates to be used during the next comparison at block 306.

The situation may arise in which the highest matching template for each sensing vector does not correspond to the same posture for any other sensing vector. In this case, the posture associated with a template yielding the highest morphology match overall for all selected or all available ECG sensing vectors may dictate the first templates selected for the next comparison at block 306. Alternatively, the highest matching template for each sensing vector may be selected as the first vector to be used for the next comparison regardless of the conflicting patient postures associated with those templates.

The selection of the first template(s) to be used for the next comparison at block 306 may be based on the highest matching scores during the detected SVT. Alternatively, template selection at block 311 may be performed after the heart rhythm has returned to a lower, resting heart rate that is below a VT detection rate zone.

If none of the ECG signals from selected sensing vectors match the selected templates for each respective sensing vector at block 308, the cardiac signal analyzer 90 determines if another template is available for any of the sensing vectors at block 310. If at least one additional stored template is available, a next set of templates is selected at block 316 corresponding to a different patient posture than the first set of templates. The next set of templates is compared to the respective ECG signals received during the unknown rhythm. This process continues until all stored templates have been utilized or SVT is detected.

If all stored templates have been compared to the respective sensing vector signals without meeting SVT detection criteria, VT is detected at block 312. The ICD 14 delivers a therapy to treat the VT at block 314. A cardioversion shock may be delivered. In IMD systems that include pacing capabilities, ATP may be delivered.

The SVT detection criteria applied at block 308 based on stored templates are described as being secondary VT/SVT detection criteria that are applied only after a preliminary VT detection has been made based on primary VT detection criteria, such as RR interval-based criteria. In other examples, the SVT detection criteria applied to comparisons between an ECG signal during an unknown rhythm with stored morphology templates may be included in primary VT detection criteria, used with or without other primary and/or secondary detection criteria.

With reference to the example shown in FIG. 5, the first templates selected for morphology comparison at block 306 of flow chart 300 in response to a rate-based VT detection (block 304) may be templates for Posture 1. For example, if ECG1 and ECG2 are selected for ECG monitoring, a rate-based VT detection may be made at block 302 based on one or both of the selected ECG1 and ECG2 sensing vectors. Next, ECG1 Template 1,2 is compared to the cardiac signal received from ECG1 during the unknown cardiac rhythm and ECG2 Template 1,2,3,4 is compared to the cardiac signal received from ECG2 during the unknown cardiac rhythm. Both templates are associated with Posture 1 for the selected ECG1 and ECG2 sensing vectors.

If one of the two ECG1 and ECG2 signals during the unknown rhythm matches the respective ECG1 Template 1,2 or ECG2 Template 1,2,3,4 according to SVT detection criteria, SVT is detected at block 309. If neither cardiac signal meets the SVT detection criteria, the VT detection algorithm selects templates for the next patient Posture 2, which would be the same stored templates as for Posture 1 in this example (Template 1,2 for ECG1 and Template 1,2,3,4 for ECG2). As such, the VT detection algorithm selects the templates for the next patient Posture 3 at block 316. At block 308, the ECG1 cardiac signal is compared to Template 3,4. The ECG2 cardiac signal may be compared again to Template 1,2,3,4 or the previous comparison result may be used. If either cardiac signal matches the respective template corresponding to Posture 3 according to SVT detection criteria, e.g., with a matching score greater than an SVT detection threshold, SVT is detected at block 309. If both cardiac signals do not match the respective template for Posture 3, the unknown rhythm is detected as VT at block 312 since no other stored templates are available for the selected sensing vectors (ECG1 and ECG2).

As the VT/SVT detection and discrimination algorithm advances through the stored templates for each sensing vector, a new template may be selected or the same template may be used again for a given sensing vector depending on the reduced number of stored templates. At any given time, however, the templates associated with the same posture may be selected for comparing to respective ECG signals. Even though the actual patient posture may be unknown, the cardiac signals for each selected sensing vector are received simultaneously while the patient is in a given posture. Even if the patient posture changes while the ECG signals are received for multiple selected sensing vectors, the posture is the same for all sensing vectors at any given point in time.

The actual patient posture corresponding to Templates 1, Templates 2, Templates 3 and Templates 4 need not be known. All that is required, according to one example, is that all Templates 1 are generated during the same first posture for all available sensing vectors, all Templates 2 are generated during the same second posture different than the first posture for all available sensing vectors and so on. Once generated, a reduced number of stored templates may be produced. The templates stored for a given posture may be used as a set for comparing to multiple respective ECG signals from selected sensing vectors. One posture template of the reduced number of posture templates may be used in more than one group of templates when it is associated with more than one posture (due to discarding a matching template or averaging two or more generated templates).

Figure 7:
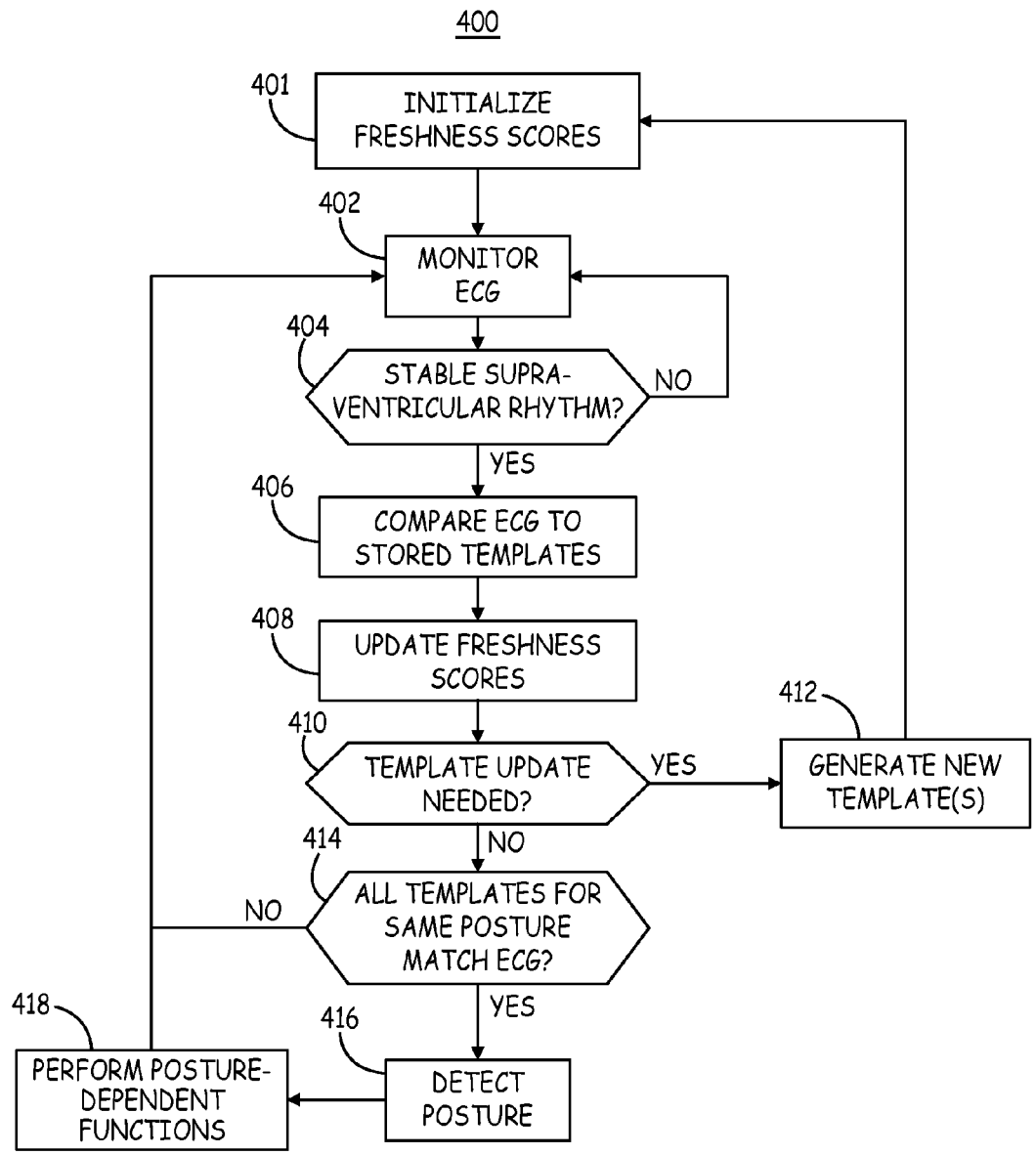
FIG. 7 is a flow chart of a method for determining when a set of stored templates should be updated.

FIG. 7 is a flow chart 400 of a method for determining when a set of stored templates should be updated. At block 401, a "freshness score" may be stored for each available sensing vector (or each individual template) as in indication of the validity of the stored templates. The validity of the template may decrease over time due to changes in the ECG signal, e.g., due to changes in the cardiac substrate, changes in medications taken by the patient, or other causes. The freshness scores are set to a starting maximum value when the templates are initially stored at block 401.

At block 402, the ECG signal is monitored from one or more available sensing vectors. A stable, supraventricular heart rhythm is detected at block 404, e.g., based on stable RR intervals and or stable ECG signal morphology with no VT or VF detection being made. The ECG signal received from each available sensing vector during the stable, supraventricular rhythm is compared to the templates stored for each respective sensing vector at block 406. The comparisons may be made over a relatively large number of cardiac cycles, e.g., at least 100 cardiac cycles, though a smaller number of cycles may be used in other instances. Comparisons between the templates and the ECG signal are performed on a scheduled periodic basis in some examples, when a stable, supraventricular rhythm has been verified. Template update criteria are applied to the results of the comparisons at blocks 408 and 410 to determine when template updates are needed.

For example, the template freshness score may be updated at block 408 for each available sensing vector in response to the comparisons made at block 406. In one example, if all templates for a given sensing vector fail to match the ECG signal during the stable, supraventricular rhythm for during one or more cardiac cycle of the stable, supraventricular rhythm, the freshness score for that sensing vector is decreased at block 408. A required number of cardiac cycle comparisons for adjusting a freshness score may be consecutive cardiac cycles, non-consecutive cardiac cycles, or non-consecutive groups of consecutive cardiac cycles.

If at least one template for a given sensing vector matches the ECG signal during the stable, supraventricular rhythm, for a required number of cardiac cycles, the freshness score may be increased for that sensing vector. It is recognized that all but one of the templates stored for a given sensing vector may correspond to the present posture of the patient. Some of the templates, therefore, may be expected to fail to match the ECG signal during the stable rhythm due to posture-dependent differences of the ECG signal, but at least one template should match the ECG signal reliably over a large number of cardiac cycles if the set of templates is still valid.

In addition to decreasing or increasing the freshness score for a given sensing vector based on ECG signal comparisons, the freshness score may be a time-decaying freshness score. For example, the freshness score may decay by a predetermined amount on a daily, weekly or monthly basis. At block 410, the freshness score is compared to a template update threshold. If the freshness score for any of the available sensing vectors falls below the update threshold, one or more new templates are generated at block 412. In one example, the templates for at least that sensing vector (or all available sensing vectors) are updated using the method described in conjunction with FIG. 4.

In another example, if the ECG signal during the stable, supraventricular rhythm consistently does not match any of the existing templates stored for a given sensing vector, e.g., based on less than 70% or another percentage of evaluated cardiac cycles not matching any of the existing templates, one new template is generated for that sensing vector at block 412 during the stable rhythm. The new template may be generated without determining the posture of the patient. In other cases, the new template may be generated in conjunction with an indication of the patient posture from external device 40 or from a posture sensor.

In some examples, the new template is stored with the existing templates already stored for that sensing vector by replacing the existing, stored template that has the lowest freshness score for that sensing vector. The template having the lowest freshness score is determined to be obsolete and is removed and the new template is stored for the associated sensing vector. Thus, addition of a new template for a given sensing vector may happen simultaneously with removal of a stored template having the lowest freshness score. The new template may be labeled according to a posture of the patient if known at the time of the new template generation. Alternatively, the template may be stored as a generic posture template without posture labeling and used an additional template that can be selected at block 316 of FIG. 6 for comparison to an ECG signal during an unknown rhythm.

It is recognized that the freshness scores for each available sensing vector may initially be set to a minimum starting value and be increased over time and in response to no templates matching the stable supraventricular ECG signal and decreased in response to at least one of the templates matching the stable, supraventricular ECG signal. A need for updating the stored templates is detected in response to the freshness score exceeding a template update threshold in this case.

When a posture sensor is present, a determination at block 410 that template updating is needed may result in automatic template updating at block 412. When the ICD 14 is not configured to detect patient posture using a posture sensor, the ICD 14 may generate a notification signal that is transmitted by the telemetry module 88 to the external device 40 to notify a patient or clinician that updates are needed.

In some examples, when stored templates do not need updating (block 410), the posture of the patient may be detected at block 416 based on the stored templates during stable, supraventricular rhythms. Posture is detected in response to the ECG signal matching a group of stored templates corresponding to the same posture across selected sensing vectors. One or more ICD functions may be performed at block 418 when a patient is known to be in a particular posture, such as an upright or lying posture. In other cases, a detected patient posture is stored in association with other patient physiological data and/or therapy delivery data acquired by the ICD to provide posture context to the data at block 418.

For example, it may be desirable to make physiological measurements at block 418 from physiological sensors 96 during particular patient states that correspond to particular patient postures, such as a resting state corresponding to a supine or side-lying posture or a non-resting state corresponding to an upright posture. Posture information may be useful in a variety of patient monitoring algorithms. For example, it may be desirable to track how much time a patient spends over 24 hour periods in a lying position vs. a reclined position vs. an upright position as an indication of the patient's quality of life or in relation to a patient's congestive heart failure status. Knowing a patient's posture at the time that other types of data are recorded, such as data for lead integrity monitoring, heart failure monitoring, sleep monitoring, blood pressure monitoring, thoracic impedance monitoring, cardiac rhythm episodes, patient annotated episodes or other types of patient monitoring may provide a clinician with added information useful in interpreting the data, diagnosing a patient condition and/or managing therapy. As such, the stored templates associated with different postures may be used to identify the patient's posture during a stable, supraventricular rhythm for use in enabling or triggering a posture-dependent function of the ICD 14 and/or recording contextual information with other patient monitoring data without requiring the use of a multi-axis accelerometer for detecting the patient posture.

Thus, a method and apparatus for detecting and discriminating VT and SVT have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A method performed by an implantable medical device, comprising:
sensing a first cardiac signal during a known cardiac rhythm from each of a plurality of available sensing vectors,
generating, for each of the plurality of available sensing vectors, a plurality of morphology templates of the first cardiac signal for each of a plurality of patient postures;
sensing a second cardiac signal during an unknown cardiac rhythm using one or more of the plurality of available sensing vectors;
comparing the second cardiac signal to at least a portion of the plurality of morphology templates without determining a current posture of the patient;
detecting the unknown cardiac rhythm as supraventricular tachycardia in response to the second cardiac signal matching at least one of the plurality of morphology templates;
detecting the unknown cardiac rhythm as ventricular tachycardia in response to the second cardiac signal not matching any of the plurality of morphology templates; and
delivering a stimulation therapy in response to detecting the ventricular tachycardia.

2. The method of claim 1, further comprising:
comparing the plurality of morphology templates generated for a given one of the plurality of available sensing vectors to each other; and
in response to the comparing of the plurality of morphology templates to each other, reducing a number of the plurality of morphology templates that are stored for comparing to the second cardiac signal during the unknown rhythm from a total number of the plurality of morphology templates generated to a reduced number of stored morphology templates; and
storing the reduced number of morphology templates.

3. The method of claim 2, wherein reducing the number of the plurality of morphology templates comprises:
determining whether a first one of the morphology templates and a second one of the morphology templates meet morphology matching criteria for a given one of the plurality of available sensing vectors; and
discarding one of the first one and the second one of the morphology templates in response to determining that the morphology matching criteria are met.

4. The method of claim 2, wherein reducing the number of the plurality of morphology templates comprises averaging at least two of the morphology templates generated for the given one of the available sensing vectors to obtain an averaged template and storing the averaged template.

5. The method of claim 4, wherein comparing the second cardiac signal sensed during the unknown cardiac rhythm to at least a portion of the plurality of morphology templates comprises:
- establishing supraventricular tachycardia detection criteria comprising a first threshold applied to a non-averaged template of the stored templates and a second threshold applied to the averaged template, the second threshold lower than the first threshold,
- determining whether the second cardiac signal and at least one of the averaged template and the non-averaged template satisfy supraventricular tachycardia detection criteria; and
- detecting the unknown cardiac rhythm as supraventricular tachycardia in response to the supraventricular tachycardia detection criteria being satisfied.

6. The method of claim 1, wherein comparing the second cardiac signal sensed during the unknown cardiac rhythm to at least a portion of the plurality of morphology templates comprises, for each sensing vector on which the second cardiac signal is sensed:
- selecting a first morphology template from the plurality of morphology templates generated for the respective sensing vector; and
- comparing the first morphology template to the cardiac signal sensed on the respective sensing vector during the unknown cardiac rhythm;
- wherein the first morphology template is selected based on the one of the plurality of morphology templates that matched a previous unknown rhythm.

7. The method of claim 1, further comprising:
- labeling each of the plurality of morphology templates according to an associated one of the plurality of patient postures;
- selecting two sensing vectors from the available sensing vectors for sensing the cardiac signals during the unknown rhythm;
- selecting, for each of the two sensing vectors, a first morphology template corresponding to a first posture based on the labeling and without determining the actual patient posture;
- comparing the second cardiac signal sensed on each of the two sensing vectors to the respective first morphology template associated with the respective sensing vector; and
- in response to neither of the second cardiac signals matching the respective first morphology templates for the first patient posture during the comparing, selecting, for each of the two sensing vectors, a second morphology template corresponding to a second patient posture based on the labeling and without determining the actual patient posture.

8. The method of claim 1, further comprising:
- sensing a third cardiac signal during a supraventricular cardiac rhythm for each of the plurality of available sensing vectors;
- for each of the available sensing vectors, comparing the third cardiac signal to each of the plurality of morphology templates stored for the respective sensing vector;
- determining whether an update of the plurality of morphology templates is needed in response to the comparing; and
- generating at least one new template for at least one of the available sensing vectors in response to determining that the update of the plurality of morphology templates is needed.

9. The method of claim 8, wherein determining whether the update of the plurality of morphology templates is needed comprises:
- initializing a time-decaying score to a starting value for each of the plurality of available sensing vectors;
- adjusting at least one of the time-decaying scores for the plurality of available sensing vectors in response to comparing the third cardiac signal to each of the plurality of morphology templates;
- comparing the time-decaying scores to a template update threshold; and
- determining that the update of the plurality of morphology templates is needed in response to at least one of the time-decaying scores crossing the template update threshold.

10. The method of claim 1, further comprising:
- sensing a third cardiac signal during a supraventricular cardiac rhythm using each of the plurality of available sensing vectors;
- comparing the third cardiac signal to at least a portion of the plurality of morphology templates corresponding to one posture of the plurality of patient postures;
- determining if the portion of the plurality of morphology templates corresponding to the one posture of the plurality of patient postures match the third cardiac signal; and
- detecting a posture of the patient as the one posture of the plurality of postures in response to determining that the portion of the plurality of morphology templates match the third cardiac signal.

11. The method of claim 1, further comprising:
- sensing a third cardiac signal during a supraventricular cardiac rhythm using each of the plurality of available sensing vectors;
- comparing the third cardiac signal to at least a portion of the plurality of morphology templates corresponding to one posture of the plurality of patient postures;
- determining if the portion of the plurality of morphology templates corresponding to the one posture of the plurality of patient postures match the third cardiac signal; and
- detecting a posture of the patient as the one posture of the plurality of postures in response to determining that the portion of the plurality of morphology templates match the third cardiac signal.

12. A medical device system, comprising:
- a sensing module coupled to a plurality of electrodes defining a plurality of available sensing vectors,
- a therapy delivery module coupled to the plurality of electrodes, the therapy delivery module configured to deliver a tachycardia therapy;
- a control module configured to:
  - generate, for each of the plurality of available sensing vectors, a plurality of morphology templates of a first cardiac signal received from the sensing module for each of a plurality of patient postures, the first cardiac signal received during a known cardiac rhythm;
  - receive a second cardiac signal from the sensing module during an unknown cardiac rhythm using one or more of the plurality of available sensing vectors;

compare the second cardiac signal to at least a portion of the plurality of morphology templates without determining a current posture of the patient;

detect the unknown cardiac rhythm as supraventricular tachycardia in response to the second cardiac signal matching at least one of the plurality of morphology templates;

detect the unknown cardiac rhythm as ventricular tachycardia in response to the second cardiac signal not matching any of the plurality of morphology templates; and cause the therapy delivery module to deliver a stimulation therapy in response to detecting the ventricular tachycardia.

13. The system of claim 12, wherein the control module is further configured to:

compare the plurality of morphology templates generated for a given one of the plurality of available sensing vectors to each other; and in response to the comparing of the plurality of morphology templates to each other, reduce a number of the plurality of morphology templates that are stored for comparing to the second cardiac signal during the unknown rhythm from a total number of the plurality of morphology templates generated to a reduced number of stored morphology templates; and storing the reduced number of morphology templates.

14. The system of claim 13, wherein the control module is configured to reduce the number of the plurality of morphology templates by:

determining whether a first one of the morphology templates and a second one of the morphology templates meet morphology matching criteria for a given one of the plurality of available sensing vectors; and discarding one of the first one and the second one of the morphology templates in response to determining that the morphology matching criteria are met.

15. The system of claim 13, wherein the control module is configured to reduce the number of the plurality of morphology templates by averaging at least two of the morphology templates generated for the given one of the available sensing vectors to obtain an averaged template and storing the averaged template.

16. The system of claim 15, wherein the control module is configured to compare the second cardiac signal sensed during the unknown cardiac rhythm to at least a portion of the plurality of morphology templates by:

establishing supraventricular tachycardia detection criteria comprising a first threshold applied to a non-averaged template of the stored templates and a second threshold applied to the averaged template, the second threshold lower than the first threshold, determining whether the second cardiac signal and at least one of the averaged template and the non-averaged template satisfy supraventricular tachycardia detection criteria; and wherein the control module is configured to detect the unknown cardiac rhythm as supraventricular tachycardia in response to the supraventricular tachycardia detection criteria being satisfied.

17. The system of claim 12, wherein the control module is further configured to:

for each sensing vector on which the second cardiac signal is sensed:

select a first morphology template from the plurality of morphology templates generated for the respective sensing vector; and compare the first morphology template to the cardiac signal sensed on the respective sensing vector during the unknown cardiac rhythm;

wherein the first morphology template is selected based on the one of the plurality of morphology templates that matched a previous unknown rhythm.

18. The system of claim 12, wherein the control module is further configured to:

label each of the plurality of morphology templates according to an associated one of the plurality of patient postures;

select from the available sensing vectors two sensing vectors for sensing the cardiac signals during the unknown rhythm;

select, for each of the two sensing vectors, a first morphology template corresponding to a first posture based on the labeling and without determining the actual patient posture;

compare the second cardiac signal sensed on each of the two sensing vectors to the respective first morphology template associated with the respective sensing vector; and in response to neither of the second cardiac signals matching the respective first morphology templates for the first patient posture during the comparing, select, for each of the two sensing vectors, a second morphology template corresponding to a second patient posture based on the labeling and without determining the actual patient posture.

19. The system of claim 12, wherein the control module is further configured to:

receive a third cardiac signal from the sensing module during a supraventricular cardiac rhythm for each of the plurality of available sensing vectors;

for each of the available sensing vectors, compare the third cardiac signal to each of the plurality of morphology templates stored for the respective sensing vector;

determine whether an update of the plurality of morphology templates is needed in response to the comparing; and generate at least one new template for at least one of the available sensing vectors in response to determining that the update of the plurality of morphology templates is needed.

20. The system of claim 19, wherein the control module is configured to determine whether the update of the plurality of morphology templates is needed by:

initializing a time-decaying score to a starting value for each of the plurality of available sensing vectors;

adjusting at least one of the time-decaying scores for the plurality of available sensing vectors in response to comparing the third cardiac signal to each of the plurality of morphology templates;

comparing the time-decaying scores to a template update threshold; and determining that the update of the plurality of morphology templates is needed in response to at least one of the time-decaying scores crossing the template update threshold.

21. A non-transitory, computer-readable medium storing a set of instructions which, when executed by a control module of an implantable medical device, cause the implantable medical device to:

sense a first cardiac signal during a known cardiac rhythm from each of a plurality of available sensing vectors, generate, for each of the plurality of available sensing vectors, a plurality of morphology templates of the first cardiac signal for each of a plurality of patient postures;

sense a second cardiac signal during an unknown cardiac rhythm using one or more of the plurality of available sensing vectors;

compare the second cardiac signal to at least a portion of the plurality of morphology templates without determining a current posture of the patient;

detect the unknown cardiac rhythm as supraventricular tachycardia in response to the second cardiac signal matching at least one of the plurality of morphology templates;

detect the unknown cardiac rhythm as ventricular tachycardia in response to the second cardiac signal not matching any of the plurality of morphology templates; and deliver a stimulation therapy in response to detecting the ventricular tachycardia.

* * * * *